(12) United States Patent
King et al.

(10) Patent No.: US 10,575,857 B2
(45) Date of Patent: Mar. 3, 2020

(54) PARTIALLY OVAL CAPSULE FOR RELOADABLE HEMOSTASIS CLIPPING DEVICE

(71) Applicant: BOSTON SCIENTIFIC SCIMED, INC., Maple Grove, MN (US)

(72) Inventors: Joseph W King, Waltham, MA (US); Naroun Suon, Lawrence, MA (US); Laurie A. Lehtinen, Marlborough, MA (US); Shawn Ryan, Littleton, MA (US); Norman C. May, Valrico, FL (US); Ramon Estevez, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 308 days.

(21) Appl. No.: 15/723,989

(22) Filed: Oct. 3, 2017

(65) Prior Publication Data

US 2018/0098771 A1  Apr. 12, 2018

Related U.S. Application Data

(60) Provisional application No. 62/404,992, filed on Oct. 6, 2016.

(51) Int. Cl.
*A61B 17/10* (2006.01)
*A61B 17/128* (2006.01)
(Continued)

(52) U.S. Cl.
CPC ........ *A61B 17/1285* (2013.01); *A61B 17/122* (2013.01); *A61B 17/1227* (2013.01);
(Continued)

(58) Field of Classification Search
CPC ....... A61B 17/08; A61B 17/083; A61B 17/10; A61B 17/122; A61B 17/1227; A61B 17/128; A61B 17/1285
See application file for complete search history.

(56) References Cited

U.S. PATENT DOCUMENTS 3,958,576 A  5/1976  Komiya

FOREIGN PATENT DOCUMENTS

DE  102009022271  11/2010
EP  2371302  10/2011
(Continued)

*Primary Examiner* — Melanie R Tyson
(74) *Attorney, Agent, or Firm* — Fay Kaplun & Marcin, LLP

(57) ABSTRACT

A system for treating tissue includes an applicator having a bushing and a control member and a clip assembly having a capsule with a channel extending therethrough. The channel includes proximal and distal portions. The distal portion extends distally from the proximal portion and flaring outward in a single plane to form opposing flared sections. The assembly also includes clip arms include proximal ends slidably received within the channel to move the arms between tissue receiving and tissue clipping configurations. The assembly further includes a yoke including a distal portion connected to the arms and a proximal portion configured to be connected to the member so that longitudinal movement of the member relative to the capsule moves the arms between the tissue receiving and clipping configurations. The yoke is positioned in the capsule so that the yoke is deformable in the plane in which the capsule flares outward.

9 Claims, 1 Drawing Sheet

(51) Int. Cl.
*A61B 17/122* (2006.01)
*A61B 17/08* (2006.01)
*A61B 90/00* (2016.01)
*A61B 17/00* (2006.01)
*A61B 17/12* (2006.01)

(52) U.S. Cl.
CPC ... *A61B 17/083* (2013.01); *A61B 2017/00477* (2013.01); *A61B 2017/00818* (2013.01); *A61B 2017/12004* (2013.01); *A61B 2090/037* (2016.02)

(56) References Cited

FOREIGN PATENT DOCUMENTS

| | | |
|---|---|---|
| JP | 5038691 | 4/1975 |
| WO | 2012151415 | 11/2012 |

PARTIALLY OVAL CAPSULE FOR RELOADABLE HEMOSTASIS CLIPPING DEVICE

PRIORITY CLAIM

This present disclosure claims priority to U.S. Provisional Patent Application Ser. No. 62/404,992 filed Oct. 6, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising an applicator including a bushing and a control member, the control member extending through the bushing to an enlarged distal end and a clip assembly releasably coupleable to the applicator, the clip assembly including a capsule, clip arms and a yoke. The capsule extends from a proximal end to a distal end and includes a channel extending longitudinally therethrough, the channel including a proximal portion and a distal portion, the distal portion extending distally from the proximal portion and flaring outward in a single plane to form opposing flared sections. The clip arms extend from proximal ends to distal ends, the proximal ends slidably received within the channel of the capsule to move the clip arms between a tissue receiving configuration, in which distal ends of the clip arms are separated from one another, and a tissue clipping configuration, in which distal ends of the clip arms are moved toward one another. The yoke includes a distal portion connected to the clip arms and a proximal portion configured to be connected to the enlarged distal end of the control member so that longitudinal movement of the control member relative to the capsule moves the clip arms between the tissue receiving configuration and the tissue clipping configuration, the yoke being positioned in the capsule so that the proximal portion of the yoke is deformable in the plane in which the capsule flares outward to receive the enlarged distal end therewithin.

In an embodiment, the proximal portion of the capsule may have a cross-sectional area that is substantially circular and the distal portion of the capsule has a cross-sectional area that is substantially ovoid.

In an embodiment, a major axis of the ovoid distal portion of the capsule may be larger than a diameter of the proximal portion of the capsule.

In an embodiment, a minor axis of the ovoid distal portion of the capsule may be substantially equal to a diameter of the proximal portion of the capsule.

In an embodiment, the proximal portion of the yoke may include opposed portions biased toward one another and define therebetween a space sized and shaped to receive the enlarged distal end, the opposed portions spreading apart to permit the enlarged distal to be passed distally thereinto.

In an embodiment, the opposed portions may be movable in the plane in which the distal portion of the capsule is flared so that, when the opposed portions are deflected to receive the enlarged distal end within the space, the deflected opposed portions are received within the opposing flared sections of the distal portion of the capsule.

In an embodiment, the proximal portion of the capsule may be sized and shaped so that, when the yoke is received therein, the opposed portions are prevented from being deflected to release the enlarged distal end.

In an embodiment, the proximal and distal portions of the yoke may be connected to one another via a frangible link designed to fail when a force exerted thereon exceeds a predetermined threshold value.

In an embodiment, the capsule may be releasably coupleable to the applicator via one of a snap fit and a friction fit.

The present disclosure also relates to a clipping device, comprising a pair of clip arms extending from proximal ends to distal ends, the proximal ends connected to a yoke slidably received within a channel of a capsule to move the clip arms between a tissue receiving configuration, in which distal ends of the clip arms are separated from one another, and a tissue clipping configuration, in which distal ends of the clip arms are drawn toward one another, the channel of the capsule including a proximal portion and a distal portion, the distal portion extending distally from the proximal portion and flaring outward in a single plane to form opposing flared sections, a portion of the yoke deforming into one of the flared sections to receive an enlarged distal end of a control member therein.

In an embodiment, the yoke may include a distal portion connected to the clip arms and a proximal portion configured to be coupled to a control member, the distal and proximal portions connected to one another via a frangible link designed to fail when a force exerted thereon exceeds a predetermined threshold value.

In an embodiment, a cross-sectional area of the proximal portion of the capsule may be substantially circular and a cross-sectional area of the distal portion of the capsule is substantially ovoid.

In an embodiment, the circular proximal portion and the ovoid distal portion may share a center point.

In an embodiment, the yoke may include opposed portions biased toward one another and define therebetween a space sized and shaped to receive the enlarged distal end, the opposed portions spreading apart to permit the enlarged distal to be passed distally into the space.

In an embodiment, the proximal portion of the capsule may be sized and shaped so that, when the yoke is received therein, the yoke is prevented from deforming to disengage the enlarged distal end of the control member.

The present disclosure also relates to a method for treating tissue, comprising loading a first clip assembly on an applicator by pressing an enlarged distal end of a control member of an applicator distally against a first yoke connected to proximal ends of first clip arms so that opposed portions of the first yoke deform to permit the enlarged distal end to be received therein, wherein the opposed portions deform within flared sections of a distal portion of a capsule in which the first yoke is slidably received, inserting the loaded clip assembly to a target site within a living body via a working channel of an endoscope, moving the first clip assembly between a tissue receiving configuration, in which distal ends of the first clip arms are separated from one another, and a tissue clipping configuration, in which distal ends of the first clip arms are moved toward one another, by moving the control member longitudinally relative to the locking sleeve until a target tissue is gripped therebetween, as desired, locking the first clip assembly in the tissue clipping configuration by drawing the clip arms proximally into the capsule until a locking feature thereof engages a corresponding locking feature of the capsule, and releasing the clip assembly from the applicator by drawing the control member proximally relative to the clip arms, beyond a predetermined threshold value, so that a frangible link of the first yoke fails, separating the control member from the first clip arms.

BRIEF DISCLOSURE

DETAILED DESCRIPTION

Figure 1:
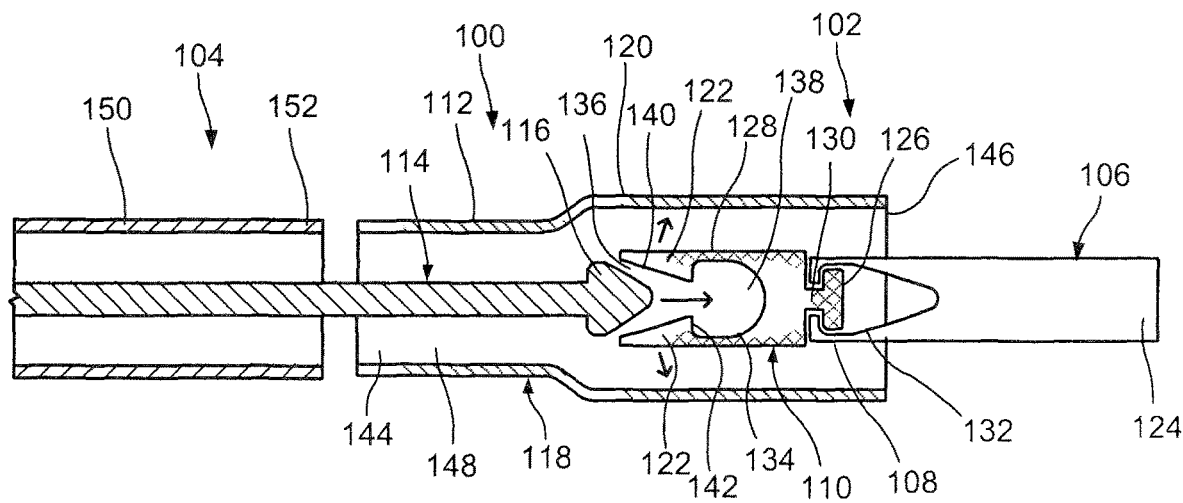
FIG. 1 shows a longitudinal cross-sectional view of a system according to an exemplary embodiment of a present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the clip assembly includes clip arms, proximal ends of which are connected to a yoke slidably received within a capsule so that the clip arms are movable between an open tissue receiving configuration and a closed tissue clipping configuration via a control wire coupled to the yoke. The yoke is coupled to an enlarged distal end of the control wire via opposed portions which are spreadable to permit the enlarged distal end of the control member to be received therein. A proximal portion of the capsule may have a substantially circular cross-sectional area while a distal portion of the capsule may have a substantially ovoid cross-sectional area so that, when the yoke is in the distal portion, the opposed portions of the yoke are permitted to spread apart to receive enlarged distal end therein, and when the yoke is in the proximal portion, the opposed portions of the yoke are prevented from spreading. Thus, when the yoke is in the proximal portion and a proximal force on the yoke via the control wire exceeds a predetermined threshold value, the yoke fractures, breaks or separates, releasing the clip assembly from the control member to deploy the clip assembly in the body.

Figure 2:
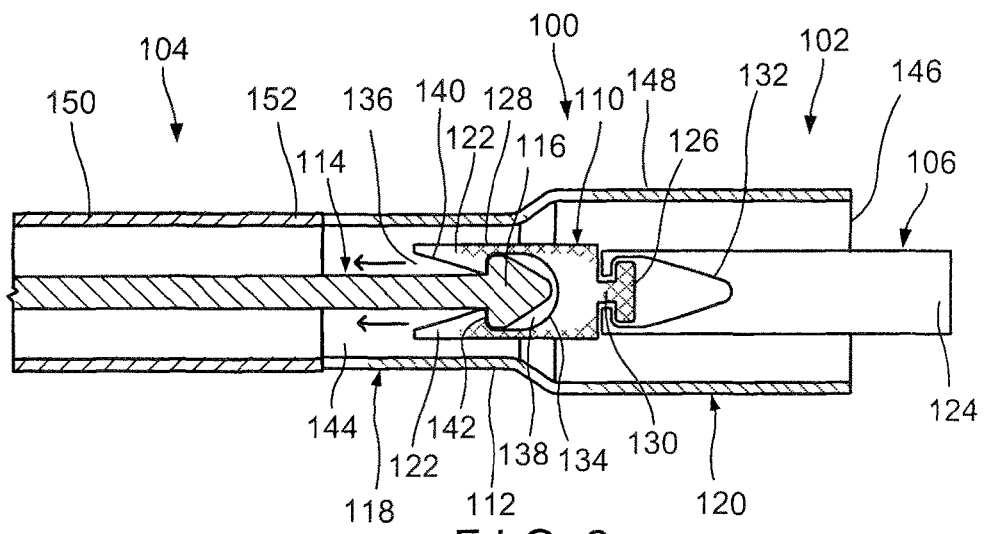
FIG. 2 shows another longitudinal cross-sectional view of the system of FIG. 1.
Figure 3:
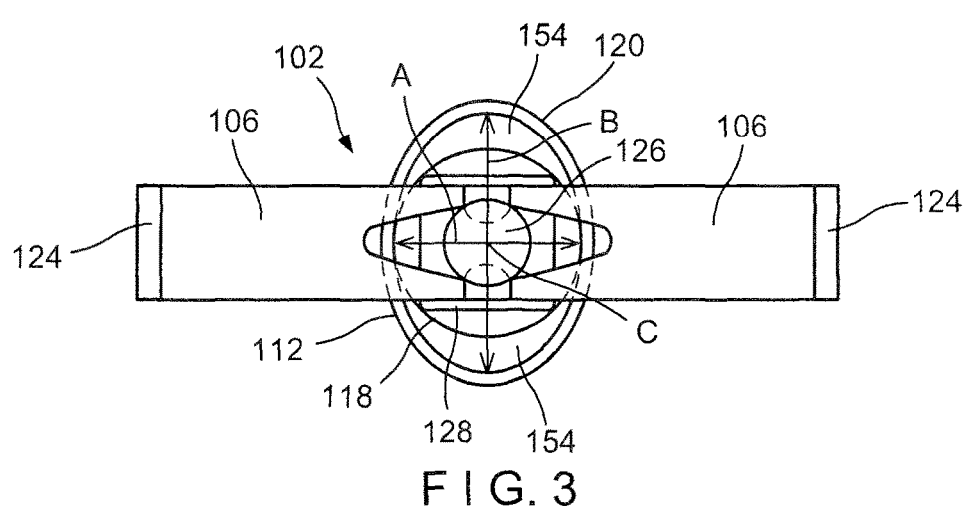
FIG. 3 shows a plan view of the system of FIG. 1 from a distal end of a capsule of the system.

As shown in FIGS. 1-2, a system 100 according to an exemplary embodiment of the present disclosure comprises a clipping assembly 102 loadable onto an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. Each clip assembly 102 according to this embodiment comprises a pair of clip arms 106, proximal ends 108 of which are coupled to a yoke 110 slidably received within a capsule 112 so that the clip arms 106 are movable between an open tissue receiving configuration and a closed tissue clipping configuration. The yoke 110 is configured to receive an enlarged distal end 116 of a control member 114 of an applicator 104 so that longitudinal movement of the control member 114 relative to the capsule 112 moves the clip arms 106 between the tissue receiving and tissue clipping configurations. The capsule 112 includes a proximal portion 118 having a cross-sectional area that is substantially circular and a distal portion 120 having a cross-sectional area that is substantially ovoid. In particular, the distal portion 120 is sized and shaped so that, when the yoke 110 is therewithin, opposed portions 122 of the yoke 110 are permitted to spread to receive the enlarged distal end 16 therein. The proximal portion 118, however, is sized and shaped so that, when the yoke 110 is drawn thereinto, the opposed portions 122 of the yoke 110 are prevented from spreading to release the enlarged distal end 116 of the control member 114. Thus, when the yoke 110 is drawn into the proximal portion 118 and a force exerted on the yoke 110 via the enlarged distal end 116 exceeds a predetermined threshold value, the yoke 110 breaks, fractures, or is otherwise separated from the clip arms 106 to deploy the clip assembly 102 in the body.

As described above, the clip assembly 102 includes the pair of clip arms 106, the proximal ends 108 of which are coupled to the yoke 110 which is slidably received within the capsule 112. Each of the clip arms 106 extends from a proximal end 108 connected to the yoke 110 to a distal end 124. The yoke 110 is configured to be connected to the control member 114 so that, when the yoke 110 and the control member 114 are connected, the control member 114 may be moved longitudinally with respect to the capsule 112 to move the clip assembly 102 between the tissue receiving and the tissue clipping configurations. The clip arms 106 of this embodiment are biased toward the open tissue receiving configuration so that, when constrained within the capsule 112, they spring to the open, tissue receiving configuration. In the tissue receiving configuration, distal ends 124 of the clip arms 106 are spread apart from one another to receive tissue therebetween. When the clip arms 106 are drawn into the capsule 112, the capsule 112 constrains the clip arms 106, drawing the distal ends 124 thereof together and holding them in the tissue clipping configuration.

As would be understood by those skilled in the art, the distal ends 124 of the clip arms 106 may include optional gripping features configured to enhance the gripping of tissue therebetween. For example, the distal ends 124 of the clip arms 106 may include tips extending laterally inward toward one another and/or teeth, protrusions, spikes or other structures configured to grip tissue between the distal ends 124 of the clip arms 106. One or both of the clip arms 106 may also include a locking feature (or complementary locking features) configured to lock the clip arms 106 in the tissue clipping configuration, once target tissue has been gripped as desired by the clip arms 106. In one embodiment, one or both of the clip arms 106 includes a locking tab extending laterally outward therefrom configured to engage a portion of the capsule 112 when the clip arms 106 have been drawn into the capsule 112 beyond a predetermined distance. For example, the locking tabs may be received within correspondingly sized, shaped and positioned locking windows extending laterally through a wall of the capsule 112 to lock the clip arms 106 relative to the capsule 112, in the tissue clipping configuration.

In one embodiment, the proximal ends 108 of the clip arms 106 may be connected to one another to form one integral piece which is connected to the yoke 110. In another embodiment, the proximal ends 108 may be connected to one another via the yoke 110. The yoke 110 includes a distal portion 126 configured to be connected to the clip arms 106 and a proximal portion 128 configured to be connected to the enlarged distal end 116 of the control member 114. The distal and proximal portions 126, 128 of the yoke 110 of this embodiment are connected to one another via a frangible link 130 that is configured to fail when a force exerted thereon exceeds a predetermined threshold value. The frangible link 130 may include, for example, a weakened portion of the yoke 110 formed via a taper, a notch, a recess or other structure decreasing a cross-sectional area of the yoke 110 therealong. In this embodiment, the distal and proximal portions 126, 128 may be integrally formed of a single piece of material. In another embodiment, the frangible link 130 may include a weld, adhesive or other coupling connecting the distal and proximal portions 126, 128. In this embodiment, the distal and proximal portions 126, 128 may be two separate elements coupled to one another via the frangible link 130.

The distal portion 126 may be connected to the arms 106 in any of a variety of ways. In one example, the distal portion 126 may be received within a correspondingly sized and shaped space 132 at the proximal end 108 of the clip arms 106 such that when the distal portion 126 is received within the space 132, the yoke 110 is substantially fixed relative thereto. Thus, movement of the yoke 110 correspondingly moves the clip arms 106.

The proximal portion 128 is configured to be connected to the enlarged distal end 116 of the control member 114 of the applicator 104 via opposed portions 122 defining a longitudinal slot 134 extending from a proximal opening 136 at a proximal end of the yoke 110 along a longitudinal axis of the yoke 110 to a distal portion 138 sized and shaped to receive the enlarged distal end 116. A proximal portion 140 of the slot 134 extending between the proximal opening 136 and the distal portion 138 has a cross-sectional area (e.g., diameter) smaller than a cross-sectional area of the distal portion 138. The opposed portions are spreadable to receive the enlarged distal end 116 and biased toward one another so that, once the enlarged end 116 passes distally into the distal portion 138 of the longitudinal slot 134, the opposed portions 122 spring back to lock the enlarged distal end 116 within the distal portion 138, coupling the control member 114 to the yoke 110. Thus, longitudinal movement of the control member 114 relative to the capsule 112 may control movement of the clip arms 106 between the tissue receiving and the tissue clipping configurations.

According to this embodiment, the enlarged distal end 116 of the control member 114 may be inserted into the distal portion 138 via the proximal opening 136 of the yoke 110. When the control member 114 is pushed distally into the yoke 110 with a force greater than a predetermined threshold value, the proximal portion 140 deforms to permit the enlarged distal end 116 to be passed therethrough into the distal portion 138. In other words, opposed portions 122 are separated from one another to permit the enlarged distal end 116 move therepast through the proximal portion 140 into the distal portion 138. Once the enlarged distal end 116 has been received within the distal portion 138, the proximal portion 140 of the slot 134 reverts to its original size, holding the enlarged distal end 116 of the control member 114 in the distal portion 138. In one embodiment, the proximal portion 140 of the slot 134 may include features facilitating passage of the enlarged distal end 116 distally therepast. For example, the proximal portion 140 may taper from the proximal opening 136 toward the distal portion 138 so that the enlarged distal end 116 is distally slidable thereagainst as the enlarged distal end 116 is being inserted into the yoke 110. Once the enlarged distal end 116 is received within the distal portion 138 of the longitudinal slot 134, the enlarged distal end 116 is prevented from being moved proximally thereoutof via a proximal shoulder 142 of the distal portion 138.

The capsule 112 extends from a proximal end 144 to a distal end 146 and includes a channel 148 extending longitudinally therethrough. The proximal end 144 may be releasably connected to the applicator 104 in any of a variety of ways. In one embodiment, the capsule 112 engages a bushing 150 of the applicator 104 in a way that permits the clip arms 106 to be moved relative to the capsule 112 from an initial insertion configuration substantially similar to the tissue clipping configuration, in which the clip arms 106 are constrained via the interior surface of the capsule 112, distally toward the tissue receiving configuration. An initial distal movement of the clip arm 106 relative to the capsule 112, from the insertion configuration to the tissue receiving configuration, may cause the capsule 112 to disengage the applicator 104. Thus, once target tissue is received between the distal ends 124 of the clip arms 106 and the clip arms 106 are drawn proximally relative to the capsule 112 to draw the clip arms 106 toward one another, the capsule 112 will also be moved proximally until the capsule 112 comes into contact with a distal end 152 of the bushing 150. Once the capsule 112 abuts the distal end 152 of the bushing 150, the clip arms 106 may be drawn further proximally relative to the capsule 112, toward the tissue clipping configuration. Upon disengagement of the control member 114 from the clip arms 106, as will be described in further detail below, the clip assembly 102 is deployed within the body. This releasable connection may be achieved via, for example, a friction fit or a loose snap connection as would be understood by those skilled in the art.

In another embodiment, the capsule 112 may be releasably connected to the applicator 104 in a way such that the capsule 112 is released from the applicator 104 upon disengagement of the control member 114 from the clip arms 106. For example, the proximal portion 118 of the yoke 110 and/or a portion of the control member 114 may interface with a coupling mechanism between the capsule 112 and the bushing 150 so that, removal of the control member 114 therefrom disengages the capsule 112 from the applicator 104 to deploy the clip assembly 102 in the body.

The channel 148 of the capsule 112 is sized and shaped to slidably receive the yoke and at least a proximal portion of the clip arms 106. In particular, the channel 148 of the capsule 112 includes the proximal portion 118 which has a substantially circular cross-section and the distal portion 120 which has a substantially ovoid cross-section. A minor axis A of the ovoid cross-section of the distal portion 120 may be substantially the same as a diameter of the proximal portion 118 while a major axis B of the ovoid cross-section is larger than the diameter of the proximal portion 118. In other words, the channel 148 of the capsule 112 may have a substantially cylindrical shape along the proximal portion 118 which flares outward in a single plane including a longitudinal axis of the capsule 112 (e.g., along major axis B) to form a substantially ovoid shape along the distal portion 120. The proximal and distal portions 118, 120 may extend coaxially relative to one, sharing a center point C, so that edges of opposing flared sections 154 of the distal portion 120 are substantially equidistant from the center point (e.g., longitudinal axis of the capsule 112).

The yoke 110 is positioned within the channel 148 so that opposed portions 122 are aligned along the major axis B. The distal portion 120 is sized and shaped so that, when the yoke 110 is received within the distal portion 120, the opposed portions 122 of the yoke 110 are permitted to spread to allow the enlarged distal end 116 to be received therein. When the yoke 110 is drawn proximally into the proximal portion 118, however, the opposed portions 122 are constrained via an interior surface thereof so that the opposed portions 122 cannot spread, thereby preventing the enlarged distal end 116 from being disengaged therefrom. Although the exemplary embodiment shows and describes the cross-sectional areas of the proximal and distal portions 118, 120 as substantially circular and ovoid, respectively, it will be understood by those of skill in the art that the proximal and distal portions 118, 120 may have any of a variety of shapes and sizes so long as the yoke 110 is permitted to open (e.g., permit passage of the enlarged distal end 116 thereinto) when within the distal portion 120 and prevented from opening (e.g., prevented from permitting disengagement of the enlarged distal end 116 from the yoke) when within the proximal portion 118. For example, in one alternate embodiment, the proximal portion 118 may have a substantially square cross-section while the distal portion 120 may have a substantially rectangular cross-section.

In addition, according to the embodiment shown, the proximal and distal portions 118, 120 of the channel 148 may be defined via an exterior shape of the capsule 112. It will be understood by those of skill in the art, however, that the exterior shape of the capsule 112 is not required to correspond to the shape of the proximal and distal portions 118, 120 of the channel 148. For example, in another embodiment, the exterior shape of the capsule 112 may be constant along an entire length thereof, with just a shape of the proximal and distal portions 118, 120 of the channel 148 varying therewithin.

Prior to being loaded on the applicator 104, the clip assembly 102 may be stored in a cartridge configured to facilitate loading of the clip assembly 102 on the applicator 104. The cartridge may be configured as a storage container defining a space therewithin that is sized and shaped to house the clip assembly 102 with the coupler 106. The clip assembly 102 may be housed within the cartridge in the tissue receiving configuration. The cartridge includes a proximal opening through which the a distal portion of the applicator 104 may be inserted to be coupled to the clip assembly 102, as will be described in further detail below. The cartridge holds the clip assembly 102 in position to facilitate loading onto the applicator 104.

The applicator 104 includes the bushing 150 or catheter, a flexible member (not shown) extending proximally therefrom, and the control member 114. A proximal end of the flexible member may be connected to a handle portion. The bushing 150 extends longitudinally from a proximal end connected to the flexible member to the distal end 152 configured to be releasably connected to the capsule 112 of the clip assembly 102. The control member 114 extends through the bushing 150 and the flexible member from the enlarged distal end 116 to a proximal end connected to an actuator of the handle portion. The flexible member may be formed as a coil or wire having sufficient flexibility to be passed through even tortuous paths of the living body and, in this embodiment, is sized and shaped to be passed through a working channel of an endoscope of other insertion device. The flexible member, however, may be formed of any other suitable flexible structure so long as the flexible member is capable of providing a force in compression sufficient to counter the tension to be placed on the control member 114 from the clip assembly 102.

An exemplary method for loading the clip assembly 102 onto the applicator 104 comprises pushing the enlarged distal end 116 of the control member 114 distally against the proximal portion 128 of the yoke 110, which may be pre-assembled with the clip assembly 102, until a distal force applied on the proximal portion 140 of the longitudinal slot 134 exceeds a predetermined threshold value, causing opposing portions 122 of the yoke 110 to deflect away from one another to permit the enlarged distal end 116 to be moved distally therepast. As described above, the opposed portions 122 are positioned so that they deflect in a plane defined by the major axis B of the ovoid distal portion 120 of the capsule 112. In other words, the deflected opposed portions 122 are received within the opposing flared sections 154 of the distal portion 120 of the capsule 112. After the enlarged distal end 116 passes the proximal portion 140 and into the distal portion 138, the proximal portion 140 reverts under its natural bias to a position to hold the enlarged distal end 116 therein. As the control member 114 is being coupled to the yoke 110, the bushing 150 may also be distally pressed against the capsule 112 to releasably couple the capsule 112 to the bushing 150.

As described above, where the clip assembly 102 is housed within a cartridge, the bushing 150 and the enlarged distal end 116 of the control member 114 may be inserted through a proximal opening of the cartridge to be coupled to the clip assembly 102, in substantially the same manner as described above. Once the bushing 150 has been releasably connected to the capsule 112 and the enlarged distal end 116 is coupled to the clip arms 106, the control member 114 may be moved proximally to draw the clip assembly 102 toward the closed, clipping configuration. The entire applicator 104 may then be moved proximally relative to the cartridge to draw the clip assembly 102 out of the cartridge, in the closed configuration, via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the tissue clipping configuration to reduce damage and facilitate its passage through the working channel. Upon reaching the site of the target tissue, the clip assembly 102 is advanced out of the distal end of the working channel by moving the control member 114 distally relative to the bushing 150, extending the clip arms 106 distally out of the capsule 112 and moving the clip arms 106 to the tissue receiving configuration. Once the target tissue has been received between the clip arms 106, the clip assembly 102 may be moved toward the tissue clipping configuration so that the target tissue is gripped between the distal ends 124 thereof. The clip arms 106 are moved toward the tissue clipping configuration by drawing the control member 114 proximally with respect to the bushing 150 and the capsule 112. Once the clip assembly 102 is in the tissue clipping configuration, the control member 114 may be drawn further proximally to lock the clip arms 106 with respect to the capsule 112. As the control member 114 is moved proximally, the yoke 110 is drawn into the circular proximal portion 118 of the capsule 112, which is sized and shaped to prevent the opposed portions 122 of the yoke 110 from spreading or deflecting to release the enlarged distal end 116 therefrom.

Thus, to deploy the clip assembly 102, the control member 114 is drawn even further proximally. Since the clip arms 106 are fixed with respect to the capsule 112 and the yoke 110 is prevented from releasing the enlarged distal end 116, the proximal motion of the control member 114 causes the distal end 116 of the control member 114 to exert a force on the yoke 110. When the force exerted on the yoke 110 exceeds a predetermined threshold value, the frangible link 130 connecting the distal and proximal portions 126, 128 of the yoke 110 fails, separating the control member 114 (which is connected to the proximal portion 128) from the clip arms 106 (which are connected to the distal portion 126). As described above, the disengagement of the control member 114 from the clip arms 106 may also release the capsule 112 from the applicator 104. Thus, the applicator 104 may be withdrawn proximally from the body, leaving the clip assembly 102 clipped over the target tissue. Upon removal of the applicator 104 from the body, the proximal portion 128 of the yoke 110, which remains attached to the enlarged distal end 116 of the control member 114, may be removed therefrom by pulling the proximal portion 126 off of the distal end 116. When a force on the proximal portion 126 exceeds a predetermined threshold force, the longitudinal slot 134 yields or deforms to allow the enlarged distal end 116 to be removed therefrom. If so desired, a new clip assembly 102 is then loaded onto the applicator 104, in the same manner as described above, so that the system may then be used to clip a second portion of tissue. This process may be repeated using the same applicator 104 as many times as needed or desired.

It will be apparent to those skilled in the art that various modifications may be made in the present disclosure, without departing from the scope of the disclosure.

What is claimed is:

1. A system for treating tissue, comprising:
   an applicator including a bushing and a control member, the control member extending through the bushing to an enlarged distal end; and
   a clip assembly releasably coupleable to the applicator, the clip assembly including:
      a capsule extending from a proximal end to a distal end and including a channel extending longitudinally therethrough, the channel including a proximal portion and a distal portion, the distal portion extending distally from the proximal portion and flaring outward in a single plane to form opposing flared sections;
      clip arms extending from proximal ends to distal ends, the proximal ends slidably received within the channel of the capsule to move the clip arms between a tissue receiving configuration, in which distal ends of the clip arms are separated from one another, and a tissue clipping configuration, in which distal ends of the clip arms are moved toward one another; and
      a yoke including a distal portion connected to the clip arms and a proximal portion configured to be connected to the enlarged distal end of the control member so that longitudinal movement of the control member relative to the capsule moves the clip arms between the tissue receiving configuration and the tissue clipping configuration, the yoke being positioned in the capsule so that the proximal portion of the yoke is deformable in the plane in which the capsule flares outward to receive the enlarged distal end therewithin.

2. The system of claim 1, wherein the proximal portion of the capsule has a cross-sectional area that is substantially circular and the distal portion of the capsule has a cross-sectional area that is substantially ovoid.

3. The system of claim 2, wherein a major axis of the ovoid distal portion of the capsule is larger than a diameter of the proximal portion of the capsule.

4. The system of claim 2, wherein a minor axis of the ovoid distal portion of the capsule is substantially equal to a diameter of the proximal portion of the capsule.

5. The system of claim 1, wherein the proximal portion of the yoke includes opposed portions biased toward one another and defining therebetween a space sized and shaped to receive the enlarged distal end, the opposed portions spreading apart to permit the enlarged distal end to be passed distally thereinto.

6. The system of claim 5, wherein the opposed portions are movable in the plane in which the distal portion of the capsule is flared so that, when the opposed portions are deflected to receive the enlarged distal end within the space, the deflected opposed portions are received within the opposing flared sections of the distal portion of the capsule.

7. The system of claim 5, wherein the proximal portion of the capsule is sized and shaped so that, when the yoke is received therein, the opposed portions are prevented from being deflected to release the enlarged distal end.

8. The system of claim 1, wherein the proximal and distal portions of the yoke are connected to one another via a frangible link designed to fail when a force exerted thereon exceeds a predetermined threshold value.

9. The system of claim 1, wherein the capsule is releasably coupleable to the applicator via one of a snap fit and a friction fit.

* * * * *